United States Patent
Jack et al.

(10) Patent No.: US 7,995,825 B2
(45) Date of Patent: Aug. 9, 2011

(54) HISTOGRAM SEGMENTATION OF FLAIR IMAGES

(75) Inventors: Clifford R. Jack, Rochester, MN (US); Peter C. O'Brien, Rochester, MN (US)

(73) Assignee: Mayo Foundation for Medical Education, Rochester, MN (US)

( * ) Notice: Subject to any disclaimer, the term of this patent is extended or adjusted under 35 U.S.C. 154(b) by 1720 days.

(21) Appl. No.: 10/115,334

(22) Filed: Apr. 2, 2002

(65) Prior Publication Data

US 2003/0009098 A1    Jan. 9, 2003

Related U.S. Application Data (60) Provisional application No. 60/281,818, filed on Apr. 5, 2001.

(51) Int. Cl.
*G06K 9/00* (2006.01)
(52) U.S. Cl. ........ 382/131; 382/128; 382/130; 382/132; 600/407; 600/410
(58) Field of Classification Search .................. 600/410, 600/419, 544, 545, 407; 324/309; 382/132, 382/155, 170, 293–4, 128, 130, 131; 128/920, 128/923, 925
See application file for complete search history.

(56) References Cited

U.S. PATENT DOCUMENTS

| | | | |
|---|---|---|---|
| 5,204,625 A | | 4/1993 | Cline et al. |
| 5,262,945 A * | | 11/1993 | DeCarli et al. ................ 600/410 |
| 5,361,763 A | | 11/1994 | Kao et al. |
| 5,425,368 A | | 6/1995 | Brandt |
| 5,754,676 A * | | 5/1998 | Komiya et al. ............... 382/132 |
| 5,768,413 A * | | 6/1998 | Levin et al. .................. 382/173 |
| 5,812,691 A | | 9/1998 | Udupa et al. |
| 6,112,112 A | | 8/2000 | Gilhuijs et al. |
| 6,430,430 B1 * | | 8/2002 | Gosche ......................... 600/410 |
| 6,567,684 B1 * | | 5/2003 | Chenevert et al. ............ 600/410 |
| 6,584,216 B1 * | | 6/2003 | Nyul et al. .................... 382/131 |

OTHER PUBLICATIONS

B. H. Brinkmann, et al., "Optimized Homomorphic Unsharp Masking for MR Grayscale Inhomogeneity Correction," IEEE Transactions on Medical Imaging, 17(2):161-171, 1998.
J. V. Hajnal, et al., "se of Fluid Attenuated Inversion Recovery (FLAIR) Pulse Sequences in MRI of the Brain," Journal of Computer Assisted Tomography, 16(6):841-844 1992.
P. Perona and J. Malik, "Scale-space and Edge Detection Using Anisotropic Diffusion," IEEE Transactions on Pattern Analysis and Machine Intelligence, 12(7):629-639, 1990.

* cited by examiner

*Primary Examiner* — Tse Chen
*Assistant Examiner* — Baisakhi Roy
(74) *Attorney, Agent, or Firm* — Quarles & Brady LLP (57) ABSTRACT

A method for classifying tissue in a magnetic resonance image, and particularly for measuring a volume of pathological tissue such as white tissue hyperintensity (leukoaraiosis) in the brain based on the segmentation of the intensity histogram of fluid attenuated inversion recovery (FLAIR) images is described. A magnetic resonance image of the brain of a subject is acquired, and a pixel intensity histogram is constructed from the image. A statistically-based regression analysis is applied to the histogram to determine upper and lower threshold values, which define different types of brain tissue, particularly normal brain, cerebral spinal fluid (CSF), or lesion.

34 Claims, 2 Drawing Sheets

HISTOGRAM SEGMENTATION OF FLAIR IMAGES

CROSS-REFERENCE TO RELATED APPLICATION

The application claims the benefit of U.S. provisional patent application Ser. No. 60/281,818, filed Apr. 5, 2001.

STATEMENT REGARDING FEDERALLY SPONSORED RESEARCH OR DEVELOPMENT

This invention was made with government support under Grant Nos. NIH-NIA-AG 11378, AG-08031, AG-06786 and AG-16574 awarded by the National Institute of Health. The United States Government has certain rights in this invention.

BACKGROUND

The present invention relates to methods for classifying tissue in magnetic resonance images (MRI), and more particularly, to a method for classifying and quantifying leukoaraiosis in the MRI image of a brain.

White matter hyperintensity (leukoaraiosis) on magnetic resonance imaging (MRI) of the brain of elderly persons is suspected to be a direct manifestation of microvascular ischemic injury in the distribution of the penetrating arteriolar vessels. A number of clinical studies have linked leukoaraiosis with cognitive impairment in the elderly, such as Alzheimer's disease and other forms of dementia. It is, therefore, desirable to be able to quantify the amount of leukoaraiosis in the brain. However, because leukoraiosis tissue is relatively small and is generally spatially non-contiguous, accurate quantification of leukoaraiosis tissue is difficult, particularly in clinical settings.

Most clinical research studies of leukoaraiosis volume employ semi-quantitative methods of viewer ranking. These methods are not automated and the results are therefore qualitative, depending significantly on the analysis of the viewer. These methods, therefore, do not provide reproducible quantitative results, and are insufficiently accurate for clinical research of aging and dementia.

Various methods of computer aided or automated methods of image segmentation and quantification of brain MRI are also known. Existing methods are capable of measuring, for example, global brain and cerebral spinal fluid (CSF) volume with high reproducibility. While acceptable when applied to these types of tissues existing methods of automated image segmentation have proved insufficiently accurate and reproducible when applied to small, spatially non-contiguous tissues, and do not provide sufficiently accurate results when applied to leukoaraiosis.

Another prior art method for classifying and quantifying brain tissue is multi-spectral segmentation. Multi-spectral segmentation algorithms are commonly used to segment and classify MS plaques, which, like leukoaraiosis, are most often located in the white matter, typically have elevated T2 signal with respect to adjacent normal brain tissue, and assume an anatomic configuration either of spatially distributed discrete foci or confluent areas of elevated signal in the periventricular white matter. In multi-spectral segmentation algorithms, two or more spatially registered MR image volumes with different contrast properties are used to define a feature-space. The images are segmented into different tissue classes based on the principle that specific tissues form clusters in feature-space. While such algorithms are effective in many situations, there are a number of disadvantages associated with these methods, particularly when applied to clinical analyses. First, to apply a multi-spectral algorithm, multiple sets of data are required, and therefore a relatively long scan time is needed. Alignment of large sets of data for registration purposes is often difficult, and can result in inaccurate results. Furthermore, due to the long acquisition time, one or more of the interleaved acquisitions is frequently out of registration with the others due to patient head motion during the acquisition, particularly when applied to the elderly or those suffering with dementia. Under these circumstances, the results of the scan may be entirely unusable. Alternatively, the results may be blurry but "usable", again resulting in an inaccurate result.

A further disadvantage of multi-spectral segmentation algorithms is that such algorithms require supervision. Supervised algorithms require a trained operator to manually identify training sets of the major tissue classes of interest, for example CSF, brain, and leukoaraiosis lesion for each new set of images. The final result of a supervised classifier is highly dependent on operator-defined tissue classification input values which are unique to each data set. Small differences in operator judgment about the training dataset(s) may produce wide variation in results.

There remains a need, therefore, for an accurate, reproducible, and automatic method for measuring leukoaraiosis and whole brain volume in elderly subjects.

SUMMARY OF THE INVENTION

The present invention is a method for classifying tissue in a magnetic resonance image, comprising the steps of constructing a pixel intensity histogram of the magnetic resonance image and applying a statistical regression analysis to the histogram to determine a pixel intensity threshold value. The threshold value is used to segment the histogram into at least two regions, wherein at least one of the regions is representative of a tissue of interest.

A general object of the invention is to segment the histogram of a magnetic resonance image into regions using a statistically-based regression analysis. The statistically-based regression analysis comprises identifying a central portion of the histogram, determining statistical parameters of the central portion, and applying the statistical parameters as independent variables in a regression equation to calculate threshold values. The regression analysis results in a threshold value which may be employed to segment image pixels representative of a first type of tissue from those representative of a second type of tissue.

Another object of the invention is to classify a volume of pathological tissue or lesion in the brain. A Fluid Attenuated Inversion Recovery (FLAIR) image of the brain is acquired, and a pixel signal intensity histogram of the image is constructed. The histogram is segmented into three regions characteristic of leukoriaosis, normal brain tissue, and cerebral spinal fluid, and the volume of each type of brain tissue is determined.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

GENERAL DESCRIPTION OF THE INVENTION

The present invention is a method and apparatus for automatically measuring the volume of tissue in a region of interest by acquiring a magnetic resonance image, constructing a pixel intensity histogram of the image, and segmenting the histogram using a statistical regression analysis to determine threshold levels. The threshold levels define pixel intensity boundaries between classes of tissue, and are used to classify different types of tissue. The threshold levels are determined individually for each slice in an image volume and thus provide accurate classification results despite slice to slice variation in the images.

The magnetic resonance images are preferably images of the brain acquired using a Fluid Attenuated Inversion Recovery (FLAIR) imaging technique. The FLAIR image is essentially a T2-weighted image resulting in an image in which pathological tissue in the brain appears as the brightest tissue type. Because of this contrast property, FLAIR images are well-suited for automated segmentation and classification of pathological tissues such as leukoaraiosis. However, other imaging techniques, and in particular imaging techniques in which pathological tissue is characterized by an elevated T2 signal as compared to the T2 of normal brain tissue, could also be used.

Figure 3:
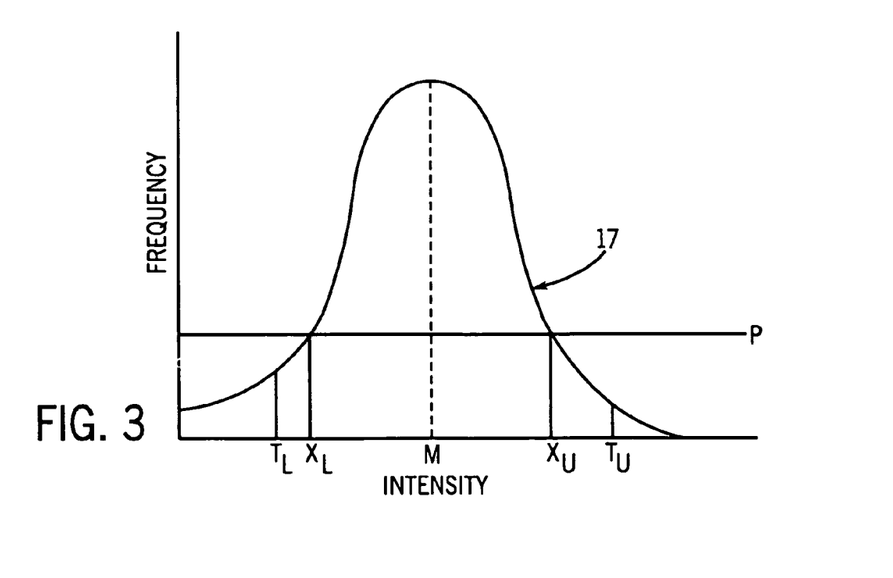
FIG. 3 is a line drawing of the intensity histogram of a FLAIR image acquired with the MRI system of FIG. 1 after the skull/scalp portion of the image has been stripped away.

After the image is acquired, a pixel intensity histogram is constructed from the FLAIR image. As well known in the art, such a histogram is produced by counting the number of image pixels at each possible image intensity level and plotting the result as a frequency versus intensity graph as shown in FIG. 3. To segment the histogram, a consistently identifiable statistical characteristic which can be, for example, a mean, a median, a mode, or other parameter is identified, and statistical parameters are calculated for the identifiable statistical characteristic. Here, a central portion representative of a central peak of normal brain tissue is identified in the histogram, and statistical parameters such as a skewness, kurtosis, mean, and mode are calculated for the central portion. The statistical parameters are then applied as independent variables in a regression analysis to determine the threshold values.

After segmentation of the histogram, the threshold values are used to classify the pixels in the histogram into three regions representing leukoraiaosis, normal brain, and cerebral spinal fluid (CSF), each of which occupy distinct regions of the intensity histogram of the FLAIR image. The markedly different signal intensity characteristics of each of these tissue types on FLAIR images enables accurate tissue volume measurement based on segmentation and statistical analysis of the intensity histogram of FLAIR images alone. The results, therefore, can be used to quantify the volume of leukoaraiosis, total brain tissue, or tissue of all three categories. Similar methods can be used to identify multiple sclerosis, cerebral infraction, brain injury, tumors and other types of pathological tissue.

The FLAIR histogram segmentation (FLAIR-histoseg) offers a number of advantages as compared to prior art systems. The FLAIR-histoseg method is a quantitative method that requires no operator input to segment the image. Furthermore, the method provides tissue classification using a single image volume, obviating the need for registration of multiple image datasets, and providing estimation of leukoaraiosis lesion volume even in the presence of intra-image rotational motion in the acquired data.

DETAILED DESCRIPTION OF A PREFERRED EMBODIMENT OF THE INVENTION

Figure 1:
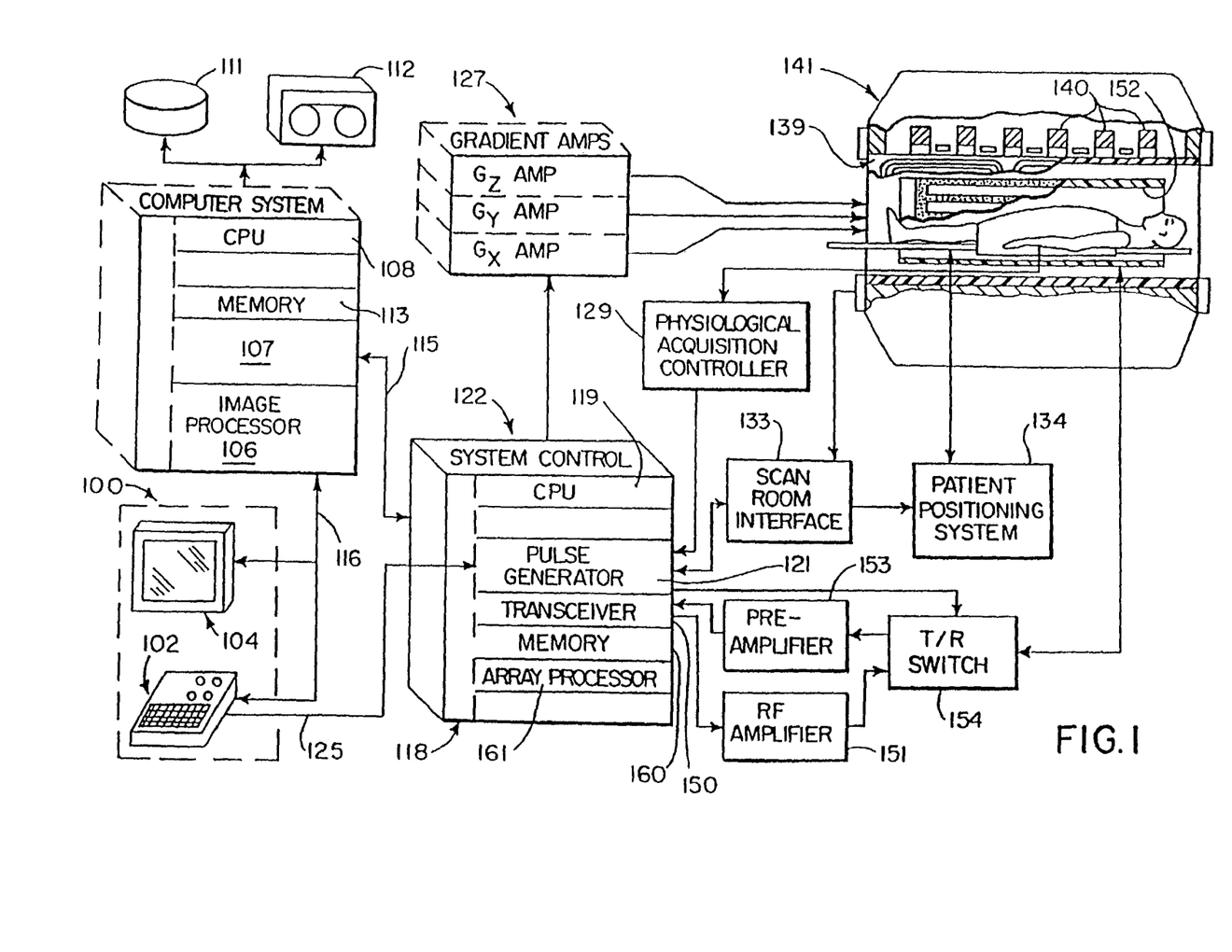
FIG. 1 is an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
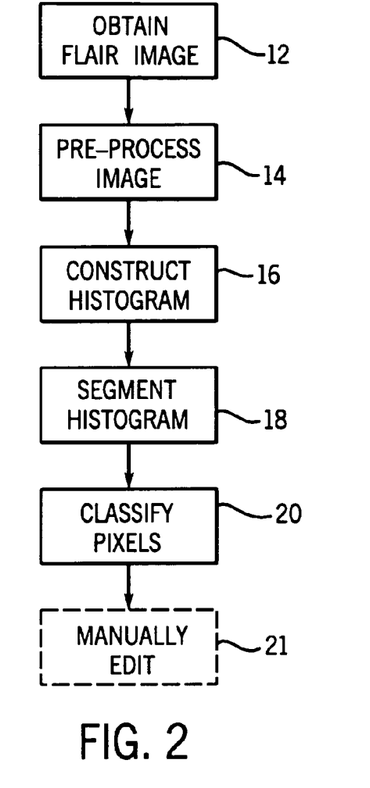
FIG. 2 is a flow chart illustrating process steps in a preferred embodiment of the present invention.

Referring now to FIGS. 1 and 2, to perform the method of the present invention a standardized scan protocol is initially applied to a patient through the pulse generator 121. The scan protocol is designed to acquire a FLAIR image generally comprising a T2 weighted image with the signal of CSF nulled, as shown in process step 12 of FIG. 2. Preferably, the following FLAIR sequence described by Hajnal, et al., "Use of Fluid Attenuated Inversion Recovery (FLAIR) Pulse Sequences in MRI of the Brain", *Journal of Computer Assisted Tomography*, 16(6):841-844, November/December, 1992 is applied with the following scan parameters: TR=11 sec, T1=2600 msec, TE=142 msec, bandwidth±32 kHz, echo train length 22, 256×192 matrix, 24 cm FOV, 3 mm interleaved slices with no interslice gap. Although a preferred sequence for obtaining the FLAIR image is described, other sequences will be apparent to those of ordinary skill in the art.

Once images of the brain are acquired, the FLAIR histogram segmentation (FLAIR-histoseg) method is applied to the data. Referring still to FIG. 2, the FLAIR histogram segmentation method basically comprises four steps: (1) preprocessing to remove artifacts and improve the quality of the image (process step 14); histogram construction (process step 16); segmentation of the histogram into tissue classification regions (process step 18); and pixel classification (process step 20). Optionally, the classification results are edited as described below (process step 21). Each of these steps are described more fully below.

In the preprocessing step 14, standard image preprocessing steps are performed in order to reduce artifacts and improve the quality of the acquired image data prior to image segmentation and classification. These include the following, and preferably performed in this order: (1) manual editing of the image to remove skull, scalp, and flow related artifacts; (2) 2D image inhomogeneity correction by a mean filter (see Brinkman B, Manduca A, Robb R. *Optimized homomorphic unsharp masking for MR grayscale inhomogeneity correction*, IEEE Trans Med Img 1998; 17:161-171, hereby incorporated by reference herein for its description of this process); (3) surface erosion with a 3×3 structure element to remove limbic cortex which has a higher intensity signal than normal brain tissue; and (4) anisotropic filtering to reduce image noise while preserving edge contrast (see Perona P, Malik J. *Scale-space and edge detection using anisotropic diffusion*, IEEE Trans Med Img 1990:12:629-639, hereby incorporated by reference herein for its description of this process). Other preprocessing steps and methods will be apparent to those of skill in the art.

Following the preprocessing 14 above, the histogram of the acquired FLAIR image is constructed in process step 16. An example is shown in FIG. 3. The histogram comprises a plot 17 of the number of pixels (i.e. frequency) of the FLAIR image in a region of interest (ROI) at each possible image intensity. The histogram contains a single central peak which corresponds to normal brain pixels. Leukoaraiosis lesion occupies the right-hand tail of this plot 17 and CSF and other background pixels occupy the left-hand tail.

Next, a fully automated statistically based method is applied to accomplish segmentation 18 of the histogram into tissue regions classified as lesion, CSF, and normal brain. To classify these tissue, upper ($T_U$) and lower ($T_L$) threshold values are calculated, as described below. These threshold values define the threshold pixel intensity levels for lesion (greater than $T_U$) and CSF (less than $T_L$). All of the remaining pixels define normal brain. The statistically determined values $T_L$ and $T_U$, therefore, can be used to quantify the volume of leukoaraiosis in the brain of the subject.

Figure 4:
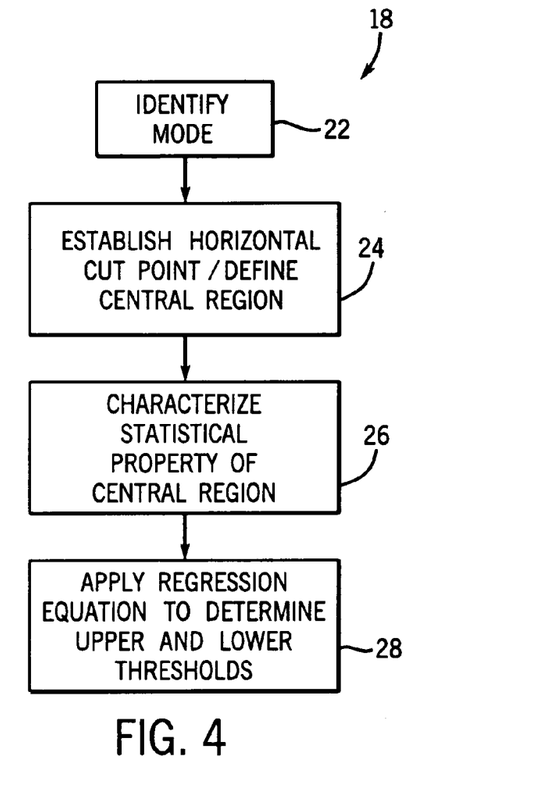
FIG. 4 is a flow chart illustrating a preferred embodiment of a segmentation step in the process of FIG. 2.

Referring now to FIG. 4, the first step of the segmentation portion 18 of the method comprises identifying a consistently identifiable statistical characteristic of the histogram which can be a mean, a median, a mode, or other parameters, depending on the type of pathological tissue to be characterized. Here the consistently identifiable statistical characteristic is the mode or maximum value M in the histogram (process step 20). After the mode is identified, in process step 24 a horizontal cut point (labeled P in FIG. 3) is established at a pre-selected fraction of the mode value, here selected to be ⅓ of the height of the mode value M (Z7). The intensities at which the horizontal cutoff value P, (Z9) intersects the histogram are denoted as the upper and lower intersection values $X_L$ and $X_U$, and the pixels in the intensity histogram which lie in the interval between $X_L$ and $X_U$ define a central portion or peak of the histogram which represents normal brain tissue. Next, in process step 26, statistical properties of the central portion of the histogram are determined for use in the regression analysis. In particular, five statistical parameters, including mean (Z1), skewness (Z3), standard deviation (Z2), kurtosis (Z4), and the total number of pixels in the central portion of the histogram (Z10) are calculated.

In process step 28, the statistical parameters, and the values $X_L$ and $X_U$ are used as independent variables in a regression equation analysis to determine the threshold values $T_L$ and $T_U$. For convenience, the following variables were also defined for use in the calculation: Z5=$X_U$–Mode; Z6=Mode–$X_L$; Z8=frequency at Mode, or the number of pixels with the Mode value.

To determine $T_L$ and $T_U$, regression equations were derived as described in the section entitled Development of the Method, below. To determine $T_L$ the following equation is applied:

$$T_L = -2118.4 - 1.306(Z_3) - 7065.7(Z_4) + 18.5\left(\frac{Z_6}{Z_2}\right) + 0.4(X_L) - 7672.7(Z_4)^2 - 2828.7(Z_4)^3. \quad \text{Eqn. 1}$$

$T_U$ is obtained by calculating the number of pixels V in the histogram to the right of $T_U$ (i.e. the estimated volume of leukoaraiosis in that imaging section) based on the number of pixels $V^*$ to the right of $X_U$. It was determined experimentally that results were best if two different equations for V were used depending on the computed value of $V^*$ (defined as the number of pixels in the histogram to the right of $X_U$ (FIG. 3)). If $V^* \geq 3000$ pixels then:

$$\ln V^* = -3.513 + 0.007 Z_1 - 0.004 Z_8 - 0.129 V^*(10^{-3}) + 1.861(\ln V^*) \quad \text{Eqn. 2}$$

If $V^* < 3000$ pixels then:

$$\ln V = -13.969 - 0.038 Z_2 - 0.009 Z_8 - 1491 Z_9 + 0.032 X_U + 3.906 \ln P + 1.936 \ln V^* \quad \text{Eqn. 3}$$

Referring again to FIG. 2, upon completion of the regression analysis, pixels with intensity values greater than Tu are classified in process step 20 as pathological tissue or leukoaraiosis, less than $T_L$ as CSF, and between $T_L$ and $T_U$ as normal brain (FIG. 3). The number of pixels in each region determine the volume of each type of tissue in the brain, and the total brain volume.

The values $T_L$ and $T_U$ are established uniquely for each acquired imaging slice. Thus, the approach described above is able to accommodate slice to slice variation in statistical properties of the intensity histogram when determining the values ($T_L$ and $T_U$) which are used to segment the histogram. Furthermore, classification can be accomplished using a single image volume, obviating the need for registration of multiple image datasets. Therefore, estimation of leukoaraiosis lesion volume can be accomplished even in the presence of some intra-image rotational motion in the acquired data.

Referring still to FIG. 3, upon completion of segmentation and classification of the histogram an optional manual edit of the classified result can be provided to re-classify incorrectly classified pixels prior to recording leukoaraiosis and brain volume as shown in process step 21. The signal intensity of allocortex, for example, can be higher than that of isocortex on FLAIR images. Some limbic cortical areas typically have signal intensity that overlaps the intensity range occupied by leukoaraiosis. Areas in the posterior limb of the internal capsule may normally appear bright on FLAIR images as well. Central gray nuclei in which dense physiologic mineral deposition has occurred overlap the intensity range of CSF. Each of these types of tissue can be re-classified in a manual edit to correct errors in the results.

Development of the Method

To develop the regression equations 1 through 3 above, a number of synthetic or phantom images exhibiting varying levels of leukoaraiosis were developed based on sample real-life images. These phantom images provided a known leukoaraiosis volume which was used in a stepwise regression analysis with statistical parameters in order to derive the equations, as described below.

In order to develop phantom images, realistic leukoaraiosis lesions were embedded into the FLAIR image. To generate realistic leukoaraiosis lesions, the gray scale signal intensity properties of leukoaraiosis lesions found on FLAIR images of the elderly in real life were identified based on acquired images of ten individuals with varying amounts of leukoaraiosis. All the volunteers had undergone a standardized protocol MR study which included the following FLAIR sequence TR=11 sec, TI=2600 msec, TE=142 msec, bandwidth±32 kHz, echo train length 22, 256×192 matrix, 24 cm field of view (FOV), 3 mm interleaved slices with no inter-slice gap. Measurements of the signal intensity and standard deviation of white matter, CSF, and leukoaraiosis lesion were performed at 10 different sample sites throughout the brain for each of the 10 elderly volunteers. Tissue intensity values were determined as shown in Table 1:

TABLE 1

| Tissue Intensity Values | | |
| --- | --- | --- |
| | Mean | SD |
| Normal White Matter | 156 | 13 |
| Leukoaraiosis Lesion | 342 | 25 |
| CSF | 35 | 11 |
| Lesion/White Matter Ratio | 2.2 | 0.2 |

In order to create synthetic images that had realistic spatial distributions of leukoaraiosis-like lesions, regions of interest (ROI) mimicking the anatomic distribution of leukoariosis were hand drawn on the appropriate slices of the FLAIR images by a neuroradiologist. Three different binary masks of leukoariosis were manually drawn on the multi-slice FLAIR image dataset of each subject with different volumes of lesion severity which we labeled mild, moderate, and severe. The binary ROI files of leukoaraiosis were added to the original gray scale images.

A "lesion-creating" program was then written which converted the hand drawn binary ROIs into ROIs which contained the empirically determined relative signal intensity and noise distribution characteristics of leukoaraiosis for FLAIR images. The program tapered the borders of the ROIs so that the signal intensity of the synthetic leukoariosis lesions declined linearly from the binary hand-drawn ROIs to background tissue. The result was three sets of synthetic or phantom whole brain image sets (with mild moderate, and severe lesion severity) for each subject. The synthetic phantom images were designed to incorporate the following desirable features: (1) the contrast properties of the magnetic resonance images (MRI), including the relative signal intensity and noise properties of the synthetic leukoariosis lesions, were identical to those encountered in real life; (2) the anatomic distribution of leukoariosis matched that found in elderly persons in real life; and (3) the lesion volumes were known and could serve as an objective standard of the "truth".

Next, a pixel signal intensity histogram was developed for each slice of each phantom image set. The mode value in the histogram was identified; a horizontal cut point (such as the point labeled P in FIG. 3) was established at ⅓ of the height of the mode value to provide a central portion of the histogram; and the central portion of the histogram was characterized by five standard parameters: mean, skewness, standard deviation, kurtosis, and the total number of pixels in the central portion of the histogram, as described above with reference to FIG. 3. As noted above, the boundaries of the central portion are defined by the intensities at which the horizontal cutoff value (P) intersects the histogram, and are denoted as intersection points $X_L$ and Xu. Although specific parameters were used to develop these equations, and hence in the application of the equations derived above, it will be apparent that other methods of identifying the central portion of the histogram and of characterizing the central portion could be employed. Furthermore, although five selected statistical parameters were used to characterize the central portion, the number and type of statistical parameters used could be varied in the analysis. Also as noted above, although the identification of a central portion has been described for this application, the method can be applied using other consistently identifiable statistical characteristics of the histogram. In some applications, for example, depending on the pathological tissue studied, the histogram may be bi-modal, have a negative modal, or have other identifiable parameters, such as consistent means or medians.

In order to derive the equations that most accurately predict $T_L$ and $T_U$ from the central portion of FLAIR histogram, the correct $T_L$ and $T_U$ values for each image slice of each phantom were deduced using the known values of leukoaraiosis and brain volume of each phantom dataset. $T_L$ and $T_U$ were modeled as dependent variables using the statistical parameters in the brain histogram of each slice of each of the phantom datasets as independent predictor variables. Stepwise regression was used, stepping up, with $p<0.05$ as the criteria for entry into the model. The possibility for non-linear associations and interactions were evaluated. The final equations are given as equations 1-3, above, wherein the independent variables are delineated Z1-Z10 as defined above.

When developing the segmentation method, the values of $T_L$ and $T_U$ were therefore known for each of the phantom datasets and the statistical parameters from the FLAIR histograms were treated as dependent variables in regression modeling. When using the FLAIR-histoseg method to measure leukoaraiosis volume in patients, however, the procedure is reversed. That is, $T_L$ and $T_U$ are unknown, and the statistical descriptors of the brain pixels in the central portion of the histogram (between $X_L$ and $X_U$ in FIG. 3) function as predictor variables in the calculation. Therefore, the accuracy of the FLAIR-histoseg method was then tested using a second group of synthetic phantom datasets. Nine elderly volunteers subjects were identified. Synthetic leukoaraiosis lesions of three different grades, mild, moderate, and severe were embedded in the scans as described previously. The volume of the brain and the leukoaraiosis volume was computed using the FLAIR-histoseg method. The known brain and leukoaraiosis volumes for each dataset served as the standard against which the accuracy of the results were compared.

The values that appear in Table 2 for each of the three synthetic image phantom lesion severity levels represent the absolute error (i.e., absolute value) by which the output of the FLAIR-histoseg method under or overestimated the known volume of leukoaraiosis when summed across all nine multi-slice synthetic phantom image datasets. The mean average absolute error for leukoaraiosis value was 6.6%. The mean difference between the brain volume derived from the FLAIR-histoseg method and auto-tracing of the T2-weighted brain images, across all nine data sets was 1.4% (SD 1.8%).

TABLE 2

Percent Error in Leukoaraiosis Volume Measurement

|  | Mean (%) | SD (%) |
|---|---|---|
| Mild | 4.1 | 8.1 |
| Moderate | 8.0 | 13.1 |
| Severe | 7.7 | 6.7 |
| Average | 6.6 | 9.6 |

The reproducibility of the FLAIR-histoseg method was also tested. To assess reproducibility, ten volunteers underwent two separate FLAIR imaging studies during the same MRI examination for comparison purposes. Following acquisition of an initial FLAIR sequence, each subject was removed from the scanner, the subject's head was repositioned, and the subject was placed back into the MR scanner. A second FLAIR sequence identical to the first was then acquired as a separate examination which entailed re-prescanning and re-auto-shimming. The volume of leukoaraiosis and total brain was measured using the FLAIR-histoseg method. The coefficient of variation between the two examinations across all subjects was computed.

Table 3 shows the measured brain and lesion volumes of the ten volunteers who were scanned twice. The mean test re-test coefficient of variation for leukoaraiosis volume was 1.4% (SD 0.9%) and for brain volume was 0.3% (SD 0.2%).

TABLE 3

Reproducibility

| | Brain Volume in cm³ | | | Lesion Volume in cm³ | | |
|---|---|---|---|---|---|---|
| Subject | 1st Scan | 2nd Scan | Absolute Value of the Difference Between 1st and 2nd Scan in % | 1st Scan | 2nd Scan | Absolute Value of the Difference Between 1st and 2nd Scan in % |
| 1 | 968.9 | 969.8 | 0.08 | 8.4 | 8.1 | 3.39 |
| 2 | 981.2 | 980.8 | 0.04 | 27.7 | 27.7 | 0.29 |
| 3 | 1154.3 | 1152.7 | 0.18 | 18.0 | 17.7 | 1.63 |
| 4 | 1067.9 | 1056.9 | 1.04 | 75.0 | 73.2 | 3.46 |
| 5 | 998.4 | 995.5 | 0.29 | 5.4 | 5.5 | 1.46 |
| 6 | 893.9 | 891.0 | 1.33 | 6.9 | 6.9 | 0.87 |
| 7 | 1214.4 | 1223.5 | 0.74 | 13.0 | 13.6 | 4.29 |
| 8 | 1077.1 | 1080.5 | 0.32 | 14.9 | 15.0 | 1.14 |
| 9 | 998.2 | 999.2 | 0.10 | 25.7 | 25.0 | 2.60 |
| 10 | 1188.8 | 1193.1 | 0.36 | 5.4 | 5.5 | 0.74 |

It should be understood that the methods and apparatuses described above are only exemplary and do not limit the scope of the invention, and that various modifications could be made by those skilled in the art that would fall under the scope of the invention. For example, although a specific method for deriving the regression equations has been described, other methods for identifying and statistically characterizing an identifiable characteristic or central portion of the histogram will be apparent to those of ordinary skill in the art. Furthermore, although the method has been described particularly for application to identifying leukoaraiosis in the brain, the method can be applied to determine a volume of multiple sclerosis, or other pathological tissue. Additionally, although the method has been described for analysis of brain tissue, similar methods can be applied to magnetic resonance images of other regions of interest. Also, while the invention has been described for segmenting the histogram into three regions, the method can be applied to quantify the tissue in a single region, to segment the histogram into two regions, or to identify a plurality of types of tissue based on pixel intensity values. Other variations in analysis methods will also be apparent to those of skill in the art. To apprise the public of the scope of this invention, the following claims are made:

The invention claimed is:

1. A method of classifying tissue in a magnetic resonance image, the method comprising:
    (a) acquiring a magnetic resonance image of a region of interest;
    (b) constructing a pixel intensity histogram of the magnetic resonance image; and
    (c) applying a statistical regression analysis to the histogram to determine a pixel intensity threshold value for segmenting the histogram into at least two regions, wherein at least one of the regions is representative of a tissue of interest.

2. The method as defined in claim 1, wherein step (a) comprises acquiring a Fluid Attenuated Inversion Recovery (FLAIR) image of a brain.

3. The method as defined in claim 2 further comprising the steps of:
    determining an upper and a lower threshold value with the regression analysis;
    classifying the pixels having a signal intensity greater than the upper threshold value as a pathological tissue;
    classifying the pixels having a signal intensity less than the lower threshold value as a cerebral spinal fluid; and
    classifying the pixels having a signal intensity between the upper and lower threshold values as a normal brain tissue.

4. The method as defined in claim 1, wherein step (a) comprises acquiring the magnetic resonance image using an imaging method in which pathological tissue is characterized by an elevated T2 signal as compared to the T2 of normal tissue.

5. The method as defined in claim 1, wherein the statistical regression analysis of step (c) comprises:
    (i) identifying a consistently identifiable statistical characteristic of the histogram;
    (ii) determining a statistical parameter of the consistently identifiable statistical characteristic; and
    (iii) applying the statistical parameter as an independent variable in a regression analysis to determine a threshold value to classify pixels based on pixel signal intensity.

6. The method as defined in claim 5, wherein the consistently identifiable statistical characteristic comprises a central portion.

7. The method as defined in claim 6, wherein step (i) comprises:
    identifying a mode in the histogram;
    identifying a horizontal cutoff as a fraction of the mode value; and
    identifying the central portion of the histogram between an upper and a lower intersection point at which the horizontal cutoff crosses the histogram.

8. The method as defined in claim 7, further comprising the step of applying the statistical parameter of the central portion and the upper and lower intersection points as independent variables in the regression analysis.

9. The method as defined in 1, wherein the tissue of interest is a pathological tissue.

10. The method as defined in claim 1 wherein the region of interest is the brain and the tissue of interest is leukoaraiosis tissue.

11. A statistically based method for automatically quantifying a volume of tissues of interest from a magnetic resonance image, the method comprising:
    (a) acquiring a magnetic resonance image of a part of the body;
    (b) constructing a pixel intensity histogram from the magnetic resonance image;
    (c) automatically segmenting the histogram to identify a region representing a selected type of tissue based on pixel signal intensity, wherein the automatic segmentation comprises the steps of:
        (i) identifying a central portion of the pixel intensity histogram based on a statistical property of the histogram;
        (ii) using a plurality of statistical properties of the identified central portion as independent variables in a regression analysis; and
        (iii) determining a pixel intensity threshold value for the selected type of tissue using the results of the regression analysis; and
    (d) calculating the number of pixels in the region to provide a measure of the volume of the tissue in the region.

12. The method as defined in claim 11, wherein step (i) comprises the steps of:
    identifying a mode of the histogram; and
    defining the central portion as a function of the mode.

13. The method as defined in claim 12, further comprising the step of selecting a boundary of the central portion as a fraction of the number of pixels at the mode.

14. The method as defined in claim 11, wherein step (ii) comprises using a regression variable comprising at least one of a mean, a standard deviation, a skew, a kurtosis, a distance between the mode and the threshold, the mode, a quantity of pixels at the mode, and a quantity of pixels above an upper boundary of the central portion as an independent variable in the regression analysis.

15. The method as defined in claim 11 wherein the image comprises a slice of an image volume.

16. The method as defined in claim 11, wherein the image is a Fluid Attenuated Inversion Recovery (FLAIR) image.

17. The method as defined in claim 11 wherein the image is a FLAIR image of a brain of a subject.

18. The method as defined in claim 17, further comprising the step of processing the image to remove a skull and a scalp from the image.

19. The method as defined in claim 17, further comprising the step of identifying a plurality of regions for a corresponding plurality of tissues of interest, wherein the tissues of interest include a cerebral spinal fluid (CSF) tissue, a typical brain tissue, and a pathological tissue.

20. The method as defined in claim 19, wherein the pathological tissue is characterized by an elevated T2 signal as compared to a T2 level of a normal brain parenchyma.

21. The method as defined in claim 19, wherein the pathological tissue is leukoaraiosis.

22. The method as defined in claim 19 in which the pathological tissue is multiple sclerosis.

23. The method as defined in claim 19, wherein the pathological tissue is a cerebral infraction.

24. The method as defined in claim 19, wherein the pathological tissue is a brain injury.

25. The method as defined in claim 19, wherein the pathological tissue is a tumor.

26. A method for determining a volume of leukoriaosis in a brain of a subject, the method comprising:
    (a) acquiring a Fluid Attenuated Inversion Recovery (FLAIR) image of the brain of the subject;
    (b) constructing a pixel intensity histogram of the image;
    (c) identifying a central portion of the histogram approximating normal brain tissue;

(d) determining a plurality of statistical parameters of the central portion;

(e) applying the statistical parameters in a regression analysis to determine a pixel intensity threshold identifying a boundary between normal brain tissue and leukoraiosis tissue; and (f) determining a volume of leukoraiosis based on a number of pixels having an intensity greater than the threshold value.

27. The method as defined in claim 26, further comprising the step of pre-processing the image to remove the skull and the scalp.

28. The method as defined in claim 26, wherein the statistical parameters include a mean, a skewness, a standard deviation, a kurtosis, and a number of pixels in the central portion of the histogram.

29. The method as defined in claim 28, wherein the central portion is determined as a fraction of the mode.

30. The method as defined in claim 29, further comprising the step of calculating a volume of normal brain tissue based on a number of pixels between the threshold value and the lower threshold value.

31. The method as defined in claim 28, further comprising the steps of:

applying a regression analysis to determine a lower threshold value;

determining a volume of cerebral spinal fluid (CSF) in the brain based on a number of pixels having an intensity less than the lower threshold.

32. The method as defined in claim 26, further comprising the step of identifying a mode of the histogram.

33. The method as defined in claim 26, wherein the image is a single slice of an image volume.

34. The method as defined in claim 26, wherein the image comprises a plurality of slices of an image volume, and steps (a) through (f) are performed for each slice.

* * * * *

UNITED STATES PATENT AND TRADEMARK OFFICE
CERTIFICATE OF CORRECTION

PATENT NO. : 7,995,825 B2  
APPLICATION NO. : 10/115334  
DATED : August 9, 2011  
INVENTOR(S) : Jack et al.

It is certified that error appears in the above-identified patent and that said Letters Patent is hereby corrected as shown below:

claim 4, column 11, line 34 "as" should be --is--

Signed and Sealed this
Eighteenth Day of October, 2011

David J. Kappos
*Director of the United States Patent and Trademark Office*